United States Patent
Mitusina et al.

(10) Patent No.: US 6,533,749 B1
(45) Date of Patent: Mar. 18, 2003

(54) ANGLED ROTARY TISSUE CUTTING INSTRUMENT WITH FLEXIBLE INNER MEMBER

(75) Inventors: Miro Mitusina, Ruskin, FL (US); Gary Peters, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 14 days.

(21) Appl. No.: 09/404,461

(22) Filed: Sep. 24, 1999

(51) Int. Cl.[7] .............................................. A61B 17/32
(52) U.S. Cl. ......................................... 604/22; 606/170
(58) Field of Search .................. 606/170, 171, 606/180; 604/22

(56) References Cited

U.S. PATENT DOCUMENTS

| 177,490 | A | * | 5/1876 | Fones et al. | |
|---|---|---|---|---|---|
| 4,203,444 | A | | 5/1980 | Bonnell et al. | |
| 4,445,509 | A | | 5/1984 | Auth | |
| 4,466,429 | A | | 8/1984 | Loscher et al. | |
| 4,646,738 | A | * | 3/1987 | Trott | 604/266 |
| 4,669,172 | A | | 6/1987 | Petruzzi | |
| 4,706,659 | A | | 11/1987 | Matthews et al. | |
| 5,152,744 | A | | 10/1992 | Krause et al. | |
| 5,322,505 | A | | 6/1994 | Krause et al. | |
| 5,405,348 | A | | 4/1995 | Anspach, Jr. et al. | |
| 5,488,761 | A | | 2/1996 | Leone | |
| 5,510,070 | A | | 4/1996 | Krause et al. | |
| 5,922,003 | A | | 7/1999 | Anctil et al. | |

FOREIGN PATENT DOCUMENTS

EP  0 592 249 A2  10/1993

OTHER PUBLICATIONS

Judson A. Smith Co. The Future Is Now. Let Us Be Your Competitive Edge. Circle Reader Service #42 (2 Pages).

* cited by examiner

*Primary Examiner*—Michael H. Thaler

(57) ABSTRACT

An angled rotary tissue cutting instrument includes an outer member or blade, having a rigid outer tube with proximal and distal portions connected by a bend, and an inner member or blade rotatably disposed within the outer member and including an inner tube of integral one-piece construction having a spiral cut formed therein between proximal and distal ends thereof to define a flexible region adjacent the bend, and at least one layer of a spirally wound strip of material superimposed over the spiral cut portion of the inner tube. The spiral cut preferably extends to a cutting tip at the distal end of the inner tube so that the inner member can be bent closer to the distal end thereof to access difficult to reach areas of the head and neck, and other parts of the body.

22 Claims, 2 Drawing Sheets

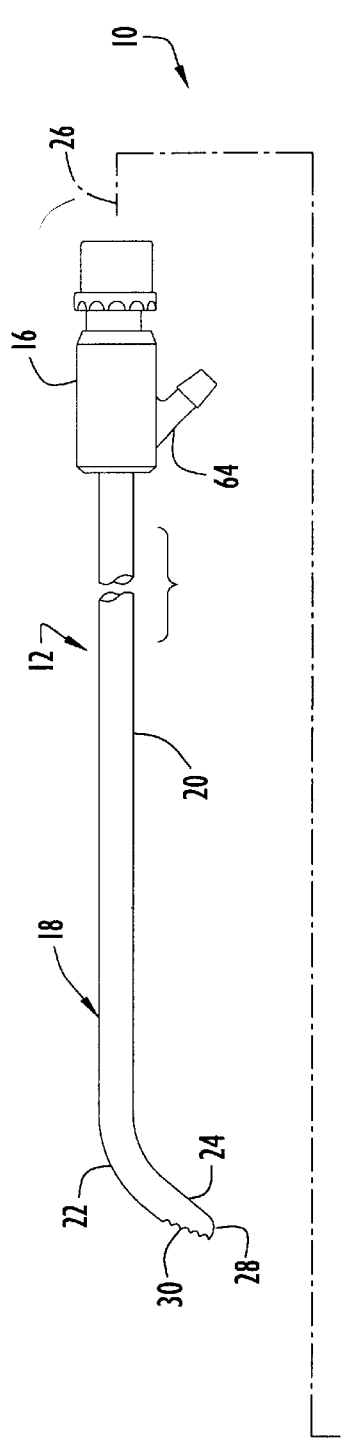
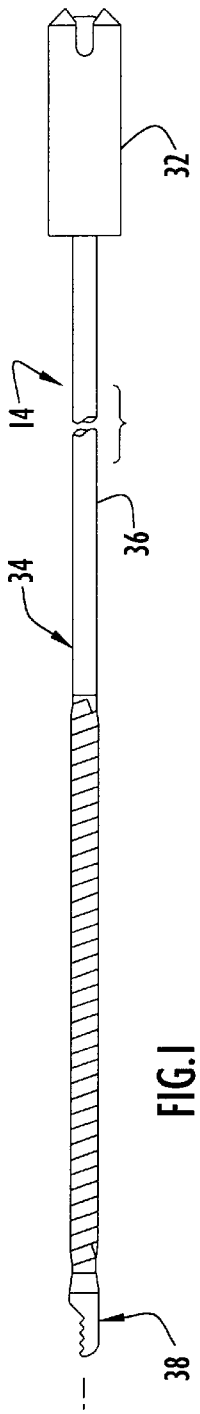
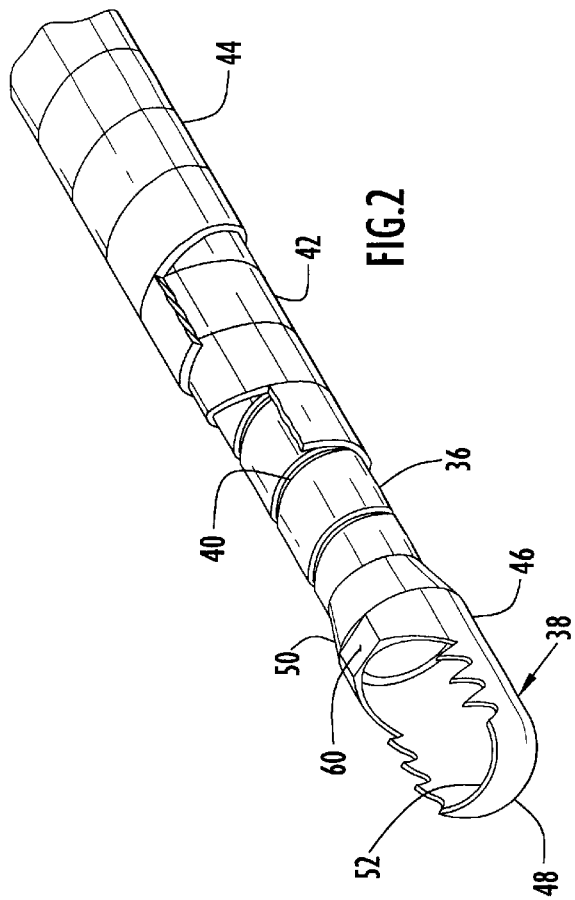
FIG.1
FIG.2

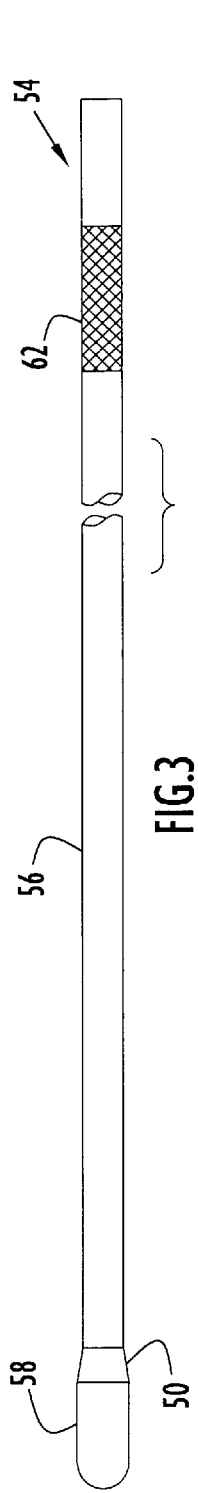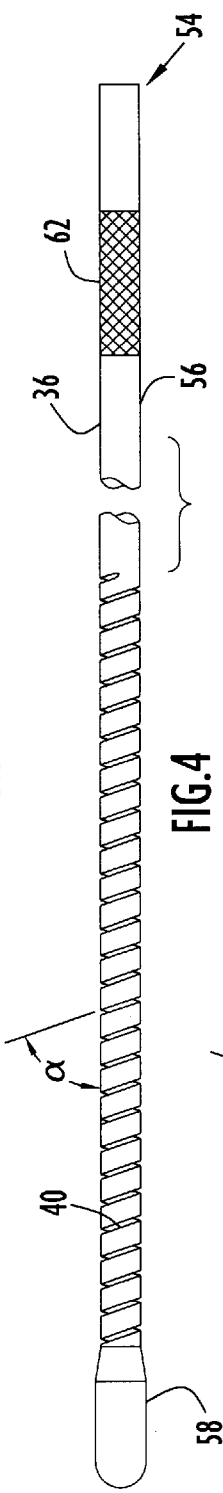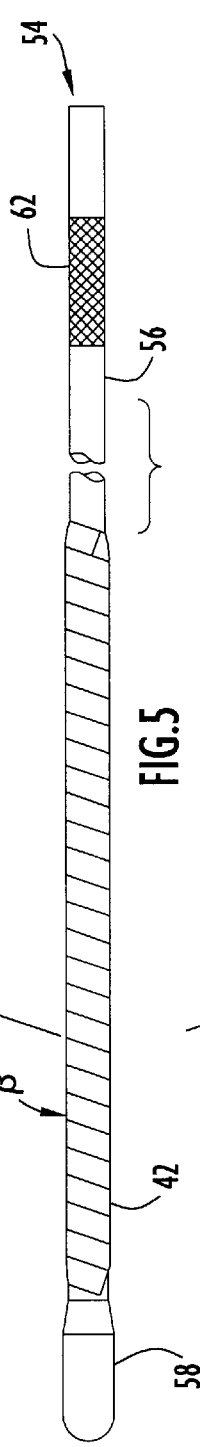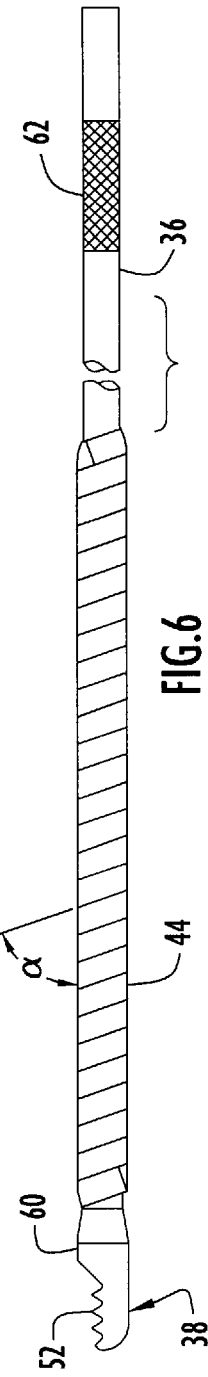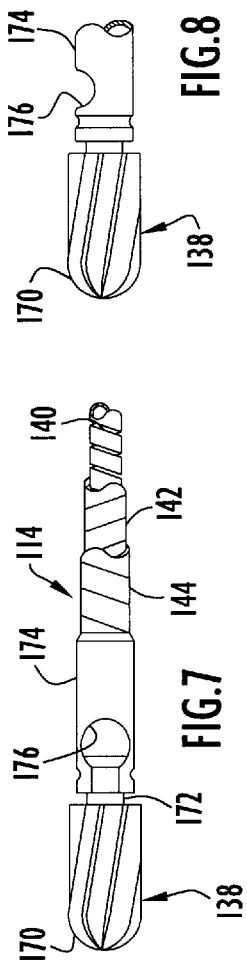

ANGLED ROTARY TISSUE CUTTING INSTRUMENT WITH FLEXIBLE INNER MEMBER

CROSS-REFERENCE TO RELATED APPLICATIONS

This application is related to application Ser. No. 09/074,739, filed on May 8, 1998, now U.S. Pat. No. 5,922,003 the disclosure of which is incorporated herein by reference.

BACKGROUND OF THE INVENTION

1. Field of the Invention

The present invention relates generally to surgical cutting instruments and, more particularly, to surgical cutting instruments having a tubular inner member with a cutting tip at a distal end rotatably disposed within a tubular outer member with a cutting window at a distal end which cooperates with or permits the cutting tip at the distal end of the inner member to cut or abrade bodily tissue.

2. Discussion of the Related Art

Surgical cutting instruments in which an elongate inner member is rotated within an elongate, tubular outer member have become well accepted in surgical procedures where access to the surgical site is gained via a narrow portal or passage. Typically, the tubular outer member includes a distal end with an opening defining a cutting port or window and the inner member includes a distal end with a cutting tip for engaging bodily tissue via the opening. Proximal ends of the inner and outer members commonly include hubs which attach to a handpiece having a motor for rotating the inner member relative to the outer member. The distal end of the inner member can have various configurations dependent upon the surgical procedure to be performed, with the opening in the distal end of the outer member being suitably configured to cooperate with the particular configuration of the distal end of the inner member to cut, resect or abrade tissue. Often the inner member is tubular so that the loose tissue resulting from a cutting, resecting or abrading procedure can be aspirated through the hollow lumen of the inner member. It is also common for the direction of rotation of the inner member to be reversible during operation. An example of a rotary tissue cutting instrument of the aforementioned type is described in U.S. Pat. No. 4,203,444 to Bonnell et al for use in performing arthroscopic knee surgery.

The tubular inner and outer members disclosed in the Bonnell et al patent are straight. In many surgical procedures, however, it is desirable for the cutting instruments to be bent or curved to access surgical sites which are generally not accessible with straight cutting instruments. For example, in arthroscopic knee surgery it is well known to use curved cutting instruments which can be positioned at various desired angles relative to the surface of the patella. While rotary tissue cutting instruments with curved or bendable shafts have been used for some time, as exemplified by U.S. Pat. No. 4,466,429 to Loscher et al. and U.S. Pat. No. 4,445,509 to Auth, these shafts typically employ a single spirally wound strip of material to impart flexibility while transmitting torque. Unfortunately, spirally wound shafts and couplings tend to unwind when rotated in a direction opposite their winding so that torque can only be transmitted efficiently in one direction.

This problem is addressed in U.S. Pat. No. 177,490 to Fones et al wherein a flexible shaft for transmitting torque in both directions is disclosed having a plurality of coaxial spirally wound strips of material wound in alternating opposite directions relative to one another. U.S. Pat. No. 4,646,738 to Trott describes a rotary tissue cutting instrument for arthroscopic surgery which is similar to the instrument described in the Bonnell et al patent but with a flexible transmission element of the type disclosed in the Fones et al patent. The flexible transmission element of Trott is made up of three coaxial spirally wound strips of material interposed between separate proximal and distal end portions of the inner member to allow the inner member to bend. Proximal and distal end portions of the inner member include reduced diameter neck portions which are telescopically received within the innermost spiral strip to facilitate welding of the strips to the other components of the inner member. Disadvantages of this arrangement include the neck portions tending to stiffen the spiral strips in the vicinity of the cutting tip thereby preventing the inner member from bending adjacent the cutting tip and the inner member having an increased diameter. In addition, it is possible for the separate components to become detached from one another during use such that torque can no longer be effectively transmitted to the cutting tip.

SUMMARY OF THE INVENTION

Accordingly, it is a primary object of the present invention to overcome the abovementioned disadvantages of the prior art and to improve angled rotary tissue cutting instruments used in surgery of the head and neck and other parts of the body.

It is another object of the present invention to reduce the number of parts needed to form an angled rotary tissue cutting instrument with tubular inner and outer members by forming a tubular portion of the inner member as an integral one-piece unit and creating a spiral cut in the tubular portion in a region adjacent a bend in the outer member.

It is yet another object of the present invention to improve access in head and neck surgery by providing an angled rotary tissue cutting instrument with a bend in an outer member immediately adjacent a cutting tip at a distal of an inner member disposed within the outer member.

Still another object of the present invention is to facilitate bending of an angled rotary tissue cutting instrument immediately adjacent the cutting tip by forming the inner member with a spiral cut which extends from a proximal portion of the inner member to the cutting tip.

The present invention is generally characterized in an angled rotary tissue cutting instrument including an outer member including a rigid tube having proximal and distal portions connected by a bend and a cutting window defined at a distal end of the tube, and an inner member rotatably disposed within the outer member and including an inner tube of integral one-piece construction with a helical cut formed therein in a first direction to define a flexible region adjacent the bend, a cutting tip disposed at a distal end of the inner tube adjacent the cutting window, and a first strip of material spirally wound over the helical cut in a second direction opposite the first direction. In a preferred embodiment, a second strip of material is spirally wound over the first strip of material in the first direction, with opposite ends of the first and second strips of material being secured to the inner tube on opposite sides of the helical cut.

Another aspect of the present invention is generally characterized in a method of fabricating an angled rotary tissue cutting instrument including the steps of producing an inner member by forming a helical cut in a first direction around an inner tube, forming a cutting tip at a distal end of the inner tube, and wrapping a first strip of material spirally over the helical cut in a second direction opposite the first direction, the inner member being inserted into the outer tube of an outer member such that the cutting tip is disposed adjacent a cutting window at the distal end of the outer tube, and bending the outer member in the vicinity of the helical cut in the inner tube. A second strip of material can also be wrapped spirally over the first strip of material in the first direction. Preferably, opposite ends of the first and second strips of material are secured to the inner tube on opposite sides of the helical cut.

Some of the advantages of the present invention over the prior art are that the number of parts needed to produce an angled rotary tissue cutting instrument are reduced, that the angled rotary tissue cutting instrument can be bent closer to the distal end or tip of the instrument to improve access in surgery of the head and neck and other parts of the body, that the size or diameter of the instrument can be minimal to increase use and access, that the inner member has a configuration to accommodate flow of irrigating fluid to the distal end, and that the strength of the flexible inner member is increased.

Other objects and advantages of the present invention will become apparent from the following description of the preferred embodiments taken in conjunction with the accompanying drawings, wherein like parts in each of the several figures are identified by the same reference numerals or by reference numerals having the same last two digits.

BRIEF DESCRIPTION OF THE DRAWINGS

FIG. 1 is a broken exploded side view of a rotary tissue cutting instrument according to the present invention.

FIG. 2 is an enlarged fragmentary perspective view, partly cut away, of the distal end of an inner member for use with a rotary tissue cutting instrument according to the present invention.

FIGS. 3–6 are broken side views illustrating a method of forming a flexible inner member for a rotary tissue cutting instrument according to the present invention.

FIGS. 7 and 8 are fragmentary top and side views, respectively, of the distal end of a modification of a flexible inner member for a rotary tissue cutting instrument according to the present invention.

DETAILED DESCRIPTION OF THE PREFERRED EMBODIMENTS

A rotary tissue cutting instrument 10 according to the present invention, as illustrated in FIG. 1, includes an outer member or blade 12 and an inner member or blade 14 rotatably received within the outer member. Outer member 12 includes a hub 16 and an outer tube 18 having a proximal portion 20 of straight configuration extending distally from the hub to a bend 22 connecting the proximal portion with a distal portion 24 oriented at an angle relative to the longitudinal axis 26 of the proximal portion. Angled portion 24 of the outer tube extends downwardly from bend 22, looking at FIG. 1, to a rounded distal end 28 having an opening facing upwardly, away from the center of curvature of the bend, to define a cutting port or window 30. The orientation of the cutting window as well as the radius of curvature, bend angle and location of the bend relative to the distal end of the angled portion are dependent upon the procedure to be performed. For example, the outer member can have any of the configurations described in U.S. patent application Ser. No. 09/074,739, filed on May 8, 1998, entitled "Angled Rotary Tissue Cutting Instrument," the disclosure of which is incorporated herein by reference.

Inner member 14 includes a hub 32 disposed proximally of the outer member hub and an elongate inner tube 34 extending distally from the hub to be disposed coaxially within the outer tube. Inner tube 34 is preferably formed as an integral one-piece unit from a medically acceptable material such as stainless steel and includes an elongate tubular portion 36 of hollow, cylindrical configuration having proximal and distal ends and a cutting tip 38 disposed at the distal end of the elongate tubular portion. Tubular portion 36 defines a lumen along the length of inner tube 34 and, as best seen in FIGS. 2 and 4, a spiral cut 40 is formed through the tubular portion between the cutting tip and the proximal end of the inner tube to define a flexible region adjacent the bend in the outer member to permit the inner member to bend while rotating within the outer member.

Spiral cut 40 is shown with a right hand turn, that is, the cut extends clockwise around the tubular portion, looking distally, and is oriented at an angle α relative to the longitudinal axis of the tubular member. The cut extends continuously without interruption and terminates immediately adjacent the cutting tip so that the inner member can be made to bend just proximally of the tip thereby facilitating use of the cutting instrument in hard to reach areas sometimes encountered in surgery of the head and neck and other parts of the body.

Inner member 14 further includes a pair of spirally wound strips 42 and 44 superimposed over the spirally cut region of the inner tube. Strips 42 and 44 are formed of an elastic material, such as stainless steel, and preferably have a rectangular cross-section allowing the strips to lay flat when wrapped around the spirally cut region of the inner tube. Innermost strip 42 is wrapped in a direction opposite that of spiral cut 40 so that it extends around the tubular portion in a counterclockwise direction looking distally, and outermost strip 44 is wrapped in a direction opposite that of the innermost strip so that it extends around the tubular portion in a clockwise direction looking distally. The innermost and outermost strips are also angled relative to one another (e.g., at supplementary angles relative to the longitudinal axis) so as to overlap one another, thereby allowing partial vacuum to be maintained in the lumen defined by the inner member. As shown, the innermost strip is oriented at an angle β which is the supplement of angle α (i.e., 180° minus α) and the outermost strip is oriented at the same angle α as the spiral cut. Opposite ends of the strips are secured to the inner tube, for example, by laser welding the ends 360° about the circumference of the inner tube, to transmit torque from a motorized handpiece (not shown) to the cutting tip while allowing the tubular portion of the inner member to conform to the angled shape of the outer member.

As best seen in FIG. 2, cutting tip 38 includes a hollow, cylindrical body 46 extending from a generally rounded distal end 48 to a frustoconical shoulder 50 of decreasing diameter in the proximal direction, the shoulder connecting the tip with the tubular portion of inner tube 34. A passage or lumen is formed longitudinally through the cutting tip, and an opening 52 is formed through side and end walls of the distal end of the cutting tip in communication with the lumen to form a suction inlet through which loose tissue can be aspirated for removal via the lumen defined by the tubular portion of the inner tube. Longitudinal edges of opening 52 form serrated cutting edges at the distal end of the cutting tip, the distal end of the cutting tip being disposed adjacent the window at the distal end of the outer member to permit the cutting edges to engage body tissue via the window.

To reduce the number of parts required to form the inner member, tubular portion 36 and cutting tip 38 of inner tube 34 are preferably formed as an integral one-piece unit from a cutter blank 54 formed of stainless steel tubing 56 with a closed elliptical end 58 as shown in FIG. 3. In a preferred embodiment, the tubing is Type 304L stainless steel tubing, ¾ hard, with an inner diameter of about 0.091 inch and an outer diameter of about 0.107 inch. The closed elliptical end preferably has an outer diameter of about 0.1330 inch, with a minor axis of about 0.0658 inch and a major axis of about 0.0720 inch. The elliptical end is preferably truncated at a proximal end to have an overall length of about 0.254 inch, or about 0.32 inch including frustoconical shoulder 50. Spiral cut 40 can be formed using any suitable technique but is preferably formed by laser cutting the tubing. In a preferred embodiment, shown in FIG. 4, the cut begins about 0.37 inch from the distal end of the elliptical end and extends proximally about 1.51 inches to terminate about 1.88 inches from the distal end of the elliptical end. As a result, inner member can be bent immediately adjacent the cutting tip. The cut is shown as a right hand spiral cut which, looking at FIG. 4, is oriented at an angle α of about 70° relative to longitudinal axis 26. The width or kerf of the cut is preferably about 0.005 inch with a longitudinal spacing of about 0.062 inch between rings formed by the spiral cut.

As shown in FIG. 5, innermost strip 42 is wrapped around the spiral cut portion of inner tube 34 in an opposite direction. In a preferred embodiment, the innermost strip is formed of Type 302 stainless steel flat strip, full hard, with a width of about 0.05 inch and a thickness of about 0.003 inch. Looking at FIG. 5, the strip is wrapped at an angle β of about 110° relative to longitudinal axis 26. Opposite ends of the strip are secured to the blank, preferably by laser welding the ends completely about the circumference of the blank.

As shown in FIG. 6, outermost strip 44 is wrapped around innermost strip 42 in the same direction as spiral cut 40. The outermost strip is preferably formed of the same material as the innermost strip and with the same configuration; however, the outermost strip is preferably oriented at the same angle α as the spiral cut. Opposite ends of the outermost strip are also preferably secured to the blank by laser welding the ends about the circumference of the blank.

Opening 52 can be formed in the elliptical end 58 to define cutting tip 38 in any suitable manner; however, it is preferred to laser cut the cutting window as shown in FIG. 6. In a preferred embodiment, three full teeth are formed along longitudinal edges of the window and a flat 60 is formed along an exterior of the cutting tip proximally of the window to permit irrigating fluid to flow over the cutting tip. Hub 32 is attached to inner tube 34 in a conventional manner using a raised fine diamond knurl 62 at the proximal end of the inner tube as a point of attachment.

The rotary tissue cutting instrument is assembled for use by inserting cutting tip 38 of inner member 14 into the proximal end of hub 16 of outer member 12 and advancing the inner member distally until the cutting tip is disposed adjacent window 52 at the distal end of the outer member. Outer member 12 can be bent at any location or locations corresponding to the spirally cut region of inner member 14. Since the spiral cut extends right up to the cutting tip, the outer member can be bent immediately adjacent the cutting window as shown in FIG. 1 to facilitate use of the instrument in difficult to reach areas of the body during surgery of the head and neck and other parts of the body.

In use, hubs 16 and 32 are connected to a conventional motorized handpiece (not shown), such as the STRAIGHT-SHOT® marketed by Xomed Surgical Products, Inc. of Jacksonville, Fla., and shown in U.S. Pat. No. 5,916,231 to Bays, the disclosure of which is incorporated herein by reference, such that the outer member 12 is held substantially stationary relative to the handpiece while permitting inner member 14 to rotate within the outer member. At this point, tubular portion 34 of the inner member is disposed concentrically within the outer member with cutting tip 38 of the inner member being disposed adjacent cutting window 30 at the distal end of the outer member and the spirally cut portion of the inner member being disposed within bend region 22 of the outer member. When the handpiece motor is actuated, outer member 12 remains substantially stationary relative to the handpiece while inner member 14 is rotated. More specifically, actuation of the handpiece motor causes hub 32 at the proximal end of the inner member to rotate. Inner tube 34 is rigidly attached to hub 32 and is thus rotated in the same direction as the hub with spiral cut 40 allowing the inner member to bend as it is rotated and spiral strips 42 and 44 reducing take-up when the direction of rotation is reversed. More specifically, if the hub is rotated in the same direction as the spiral cut, the innermost spiral strip of material wound over the inner tube will tend to unwind or expand radially and be resisted by radial contraction of the outermost spiral strip of material so that the torque can be transmitted immediately without any delay. If the hub is rotated in the direction opposite the spiral cut, the innermost spiral strip of material will tend to wind up and contract radially and be resisted by the inner tube so that torque can be transmitted immediately without any delay.

Outer member hub 16 is shown with an optional nipple 64 extending proximally from a side of the hub at an acute angle relative to the longitudinal axis of the straight portion of the outer tubular member. The nipple communicates with an annular space or channel between the inner and outer members so that, when a source of irrigating fluid is connected with the nipple, the fluid will be supplied to the cutting tip via flat 60 to prevent clogging of cut or abraded tissue being aspirated through the lumen in inner member 14. Irrigating fluid can also be provided to the cutting tip via a tube disposed externally of the outer tubular member as disclosed, for example, in U.S. Pat. No. 5,782,795, the disclosure of which is incorporated herein by reference. Suction or aspiration may be provided at the operative site via the lumen extending through the inner member.

The overall length of the rotary cutting instrument 10 as well as the location of the bend, the bend angle, radius of curvature and other dimensions are dependent upon the type of surgery to be performed. For soft tissue removal in the sinuses, for example, the rotary cutting instrument 10 preferably has an overall length between about 5.5 inches and about 6.5 inches when assembled, with a cutting window formed in the outer member and an apertured cutting tip formed in the inner member. In a preferred embodiment, the aperture or opening in the cutting tip is about 0.125 wide and about 0.25 inch long with the spiral cut terminating about 0.37 inch from the distal end of the cutting tip to permit the outer member to bend less than 0.5 inches from the distal end with a radius of curvature of between about 0.875 inches and about 1.0 inches. Cutting window 30 is shown disposed on a side of the outer tubular member opposite the center of curvature of the bend for procedures such as adenoid surgery but can be on the other side for other types of procedures such as those involving superior ethmoid access, frontal recess surgery, removal of maxillary sinus polyps, maxillary antrostomy and uncinectomy. Distal portion 24 of the outer tubular member can be oriented at any angle between about 10° and about 70° relative to proximal portion 20, but is preferably oriented at about 40° for the above procedures.

The distal end of the cutting tip can have various configurations dependent upon the surgical procedure to be performed, with the opening in the distal end of the outer member being suitably configured to cooperate with the particular configuration of the distal end of the inner member. For example, the distal end of the cutting tip can have serrated or sharp edges, can include burs, drills, trephines, or brushes, and can be configured to produce side cutting, meniscus cutting, end cutting, trimming, burring or abrading, or full radius resection. In FIGS. 7 and 8, for example, a modification of an inner member for a rotary cutting instrument according to the present invention is shown wherein the inner member 114 of the modified instrument is the same as described above but with a cutting tip 138 in the form of a bur 170. Bur 170 includes a bullet-shaped body with a plurality of flutes formed therein to define cutting surfaces; however, any suitable bur configuration can be used including, but not limited to, configurations where the bur is generally spherical, hemispherical, conical, pear shaped or cylindrical. Cutting tip 138 also includes a neck 172 extending proximally from the bur into the distal end of the inner tube. The inner tube is of integral one-piece construction with a spiral cut 140 formed therein between solid-walled tubular portions at proximal and distal ends of the tube. Distal portion 174 has an open distal end for receiving the neck of cutting tip 138, and a suction inlet can be formed by a lateral opening or hole 176 formed through a side of the distal portion in communication with the inner lumen through which tissue can be aspirated. Spiral cut 140 terminates near bur 170, for example about 0.59 inch from the distal end of the bur. The cutting tip can be attached to the inner tube in any suitable manner but is preferably inserted into the open distal end of the tube, crimped in place and laser welded. The spiral cut is similar to that described above but is shown having a left hand orientation, with innermost and outermost spiral strips 142 and 144 of material being wrapped in opposite directions around the spiral cut portion of the inner tube such that the innermost strip has a right hand orientation and the outermost strip has a left hand orientation like the cut. It will be appreciated, however, that the orientation of the spiral cut or the spiral strips can be varied in any of the above embodiments. The angle of orientation of the cut or the strips is illustrated as being the same as that described above but can also be varied.

From the above, it will be appreciated that the rotary tissue cutting instrument according to the present invention can be bent closer to the cutting tip than prior art instruments to improve access to difficult to reach areas of the body in surgery of the head and neck. The present invention also reduces the number of parts needed to produce a flexible inner member for an angled rotary tissue cutting instrument by forming a helical or spiral cut in an inner tube and wrapping one or more strips of material around the spirally cut portion of the tube to improve the torque transmitting capabilities of the tube.

The rotary tissue cutting instrument according to the present invention can be bent anywhere along the length of the outer member so long as the inner member is provided with a spiral cut located in juxtaposed relation to the bend. If desired, more complex curvatures and configurations can be formed by bending the outer member in more than one location and providing the inner member with one or more spiral cuts in juxtaposed relation to the bends.

The cutting port or window at the distal end of the outer tubular member in the rotary tissue cutting instrument according to the present invention can be defined by a distal-facing opening, a lateral-facing opening or an opening formed in both the side wall and the end wall of the outer tubular member. In addition, the window can be oriented to face towards the center of curvature of the bend or away from the center of curvature. Peripheral edges of the window can have any configuration permitting the cutting tip to cut, shave or abrade tissue including, but not limited to, configurations wherein the edges are smooth or serrated.

The spiral cut can be located anywhere along the length of the inner member dependent upon the procedure to be performed. Furthermore, more than one spiral cut can be made to accommodate more complex curvatures. The overall length of the spiral cut as well as the width or kerf of the cut and spacing between turns can be varied to control the location, radius of curvature and angle of the bend. If desired, the spirally cut portion of the inner tube can have a thinner wall thickness than other portions of the tube, for example by reducing the outer diameter of the spirally cut portion of the tube such that there is little or no protrusion of the spiral strips of material beyond the nominal diameter of the tubing. It will also be appreciated that the number of spiral strips wrapped around the spirally cut inner tube can be fewer or more than the number shown herein and that the strips can have any suitable cross-section including, but not limited to, rectangular and elliptical cross-sections. The width and thickness of the strips can be varied dependent upon the desired bend angle and amount of torque to be transmitted.

Proximal and distal portions of the outer tubular member are preferably formed as an integral one-piece unit from a relatively rigid, medically acceptable material such as Type 304 stainless steel, but can be formed of any suitable material and/or be formed separately and coupled together. The inner and outer blade member hubs can be of conventional configuration to mate with any suitable handpiece and can be made of any relatively rigid, medically acceptable material. Proximal ends of the inner and outer blade members can be provided with knurled surfaces which extend about the circumference of the members as shown in FIGS. 3–6 to mate frictionally with the hubs.

The rotary tissue cutting instrument can be adapted to accept accessories such as, for example, electrocautery, fiber optics, and laser fibers. Such accessories can, for example, be associated with the outer tube but follow the curved surfaces to the tip of the instrument.

When more than one bend is formed in the outer tubular member of the rotary tissue cutting instrument according to the present invention, the bends can be in the same plane or in different planes dependent upon the procedure for which the instrument is designed.

The features of the various embodiments described above can be combined in any manner desired dependent upon the operational requirements of the procedure to be performed and the complexity of the rotary tissue cutting instrument. It will also be appreciated that, dependent upon the cutting tip employed, the instrument of the present invention can be used to cut soft and bony tissue in humans and animals.

While the spiral cut in the inner tube has been described as being formed using laser cutting techniques, it will be appreciated that other methods can be used to form the spiral cut including, but not limited to, conventional machining with hard cutters, water jet cutting techniques, and manufacturing processes wherein the inner member is formed simultaneously with a spiral cut, e.g. by casting.

The dimensions listed above are merely exemplary and can be varied dependent upon the operational requirements of the instrument and the procedure.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. An angled rotary tissue cutting instrument comprising
an outer member including a rigid tube having proximal and distal portions connected by a bend and a cutting window defined at a distal end of said tube; and
an inner member rotatably disposed within said outer member and including an inner tube of integral one-piece construction with a helical cut formed therein in a first direction to define a flexible region adjacent said bend, a cutting tip disposed at a distal end of said inner tube adjacent said cutting window, and a first strip of material spirally wound over said helical cut in a second direction opposite said first direction.

2. An angled rotary tissue cutting instrument as recited in claim 1 wherein opposite ends of said first strip are secured to said inner tube on opposite sides of said helical cut.

3. An angled rotary tissue cutting instrument as recited in claim 2 and further comprising a second strip of material spirally wound over said first strip of material in said first direction and having opposite ends secured to said inner tube on opposite sides of said first strip.

4. An angled rotary tissue cutting instrument as recited in claim 3 wherein said first and second strips are secured to said inner tube by welding respective opposite ends of said strips 360° about a circumference of said inner tube.

5. An angled rotary tissue cutting instrument as recited in claim 3 wherein said helical cut and said second strip are each oriented at a first angle relative to a longitudinal axis of said inner tube and said first strip of material is oriented at a second angle which is the supplement of said first angle.

6. An angled rotary tissue cutting instrument as recited in claim 1 wherein said inner tube and said cutting tip are formed as an integral one-piece unit.

7. An angled rotary tissue cutting instrument as recited in claim 6 wherein said cutting tip is hollow with an opening formed therein defining a suction inlet.

8. An angled rotary tissue cutting instrument as recited in claim 7 wherein said helical cut terminates distally at said cutting tip to permit said outer member to be bent immediately adjacent said cutting tip.

9. An angled rotary tissue cutting instrument as recited in claim 8 wherein said bend is located less than about 0.5 inch from a distal end of said cutting tip.

10. An angled rotary tissue cutting instrument as recited in claim 1 wherein said cutting tip includes a bur.

11. An angled rotary tissue cutting instrument as recited in claim 10 wherein said inner tube has an open distal end and said cutting tip includes a neck extending proximally from said bur to be disposed telescopically within said open distal end of said inner tube.

12. An angled rotary tissue cutting instrument as recited in claim 11 wherein a side-facing opening is formed in said inner tube adjacent said cutting tip to define a suction inlet.

13. An angled rotary tissue cutting instrument as recited in claim 1 wherein an annular space is formed between said inner member and said outer member to define a channel for supplying irrigating fluid to said cutting tip.

14. A method of fabricating an angled rotary tissue cutting instrument comprising the steps of (a) forming an inner member by:
(i) forming a helical cut in a first direction in an inner tube;
(ii) forming a cutting tip at a distal end of the inner tube; and
(iii) wrapping a first strip of material spirally over the helical cut in a second direction opposite said first direction;

(b) forming an outer member having a rigid tube with a cutting window at a distal end;

(c) inserting the inner member into the outer member such that the cutting tip is disposed adjacent the cutting window; and (d) bending the outer member in the vicinity of the helical cut.

15. A method of fabricating an angled rotary tissue cutting instrument as recited in claim 14 wherein said step of forming a helical cut in the inner tube includes forming the helical cut such that the cut extends to the cutting tip, and wherein said step of bending the outer member includes bending the outer member immediately adjacent the cutting tip.

16. A method of fabricating an angled rotary tissue cutting instrument as recited in claim 15 wherein said step of bending the outer member includes bending the outer member less than about 0.5 inch from a distal end of the outer member.

17. A method of fabricating an angled rotary tissue cutting instrument as recited in claim 14 wherein said step of forming the inner member further includes the step of (iv) wrapping a second strip of material spirally over the helical cut in the first direction.

18. A method of fabricating an angled rotary tissue cutting instrument as recited in claim 17 wherein said step of forming the inner member further includes the steps of (v) securing opposite ends of the first strip of material to the inner tube on opposite sides of the helical cut; and
(vi) securing opposite ends of the second strip of material to the inner tube on opposite sides of the first strip of material.

19. A method of fabricating an angled rotary tissue cutting instrument as recited in claim 18 wherein said steps of securing opposite ends of the first and second strips of material includes welding the strip ends 360° about the circumference of the inner tube.

20. A method of fabricating an angled rotary tissue cutting instrument as recited in claim 14 wherein said step of forming a helical cut is performed using an inner tube of integral one-piece design.

21. A method of fabricating an angled rotary tissue cutting instrument as recited in claim 20 wherein the inner tube includes a hollow distal end and said step of forming a cutting tip includes forming an opening with cutting edges in the hollow distal end of the inner tube.

22. A method of fabricating an angled rotary tissue cutting instrument as recited in claim 20 wherein the inner tube includes an open distal end and said step of forming a cutting tip includes inserting a neck at the proximal end of a bur into the open distal end of the inner tube and forming a side-facing opening in the inner tube adjacent the cutting tip.

* * * * *